United States Patent
Kapre

(10) Patent No.: US 10,159,728 B2
(45) Date of Patent: Dec. 25, 2018

(54) MULTIVALENT VLP CONJUGATES

(71) Applicant: Inventprise, LLC, Redmond, WA (US)

(72) Inventor: Subhash V. Kapre, Redmond, WA (US)

(73) Assignee: Inventprise, LLC, Redmond, WA (US)

( * ) Notice: Subject to any disclaimer, the term of this patent is extended or adjusted under 35 U.S.C. 154(b) by 0 days.

(21) Appl. No.: 15/262,537

(22) Filed: Sep. 12, 2016

(65) Prior Publication Data

US 2017/0072043 A1 Mar. 16, 2017

Related U.S. Application Data

(60) Provisional application No. 62/216,646, filed on Sep. 10, 2015.

(51) Int. Cl.
| | |
|---|---|
| *A61K 39/385* | (2006.01) |
| *A61K 39/09* | (2006.01) |
| *C12N 7/00* | (2006.01) |
| *A61K 39/00* | (2006.01) |

(52) U.S. Cl.
CPC ............ *A61K 39/092* (2013.01); *C12N 7/00* (2013.01); *A61K 2039/5258* (2013.01); *A61K 2039/55505* (2013.01); *A61K 2039/70* (2013.01); *C12N 2730/10123* (2013.01); *Y02A 50/386* (2018.01); *Y02A 50/388* (2018.01); *Y02A 50/392* (2018.01); *Y02A 50/394* (2018.01); *Y02A 50/396* (2018.01); *Y02A 50/412* (2018.01)

(58) Field of Classification Search
None
See application file for complete search history.

(56) References Cited

U.S. PATENT DOCUMENTS

| | | | |
|---|---|---|---|
| 6,922,172 B2 | 1/2006 | Chang, et al. | |
| 7,374,766 B1 | 5/2008 | Rubido | |
| 8,784,826 B2 | 7/2014 | Borkowski et al. | |
| 9,109,007 B2 | 8/2015 | Kyle et al. | |
| 2008/0279926 A1* | 11/2008 | Vandepapeliere | A61K 39/00 424/450 |
| 2009/0081202 A1* | 3/2009 | Fischer | A61K 39/085 424/130.1 |
| 2009/0181044 A1 | 7/2009 | Apt et al. | |
| 2012/0093855 A1* | 4/2012 | Haynes | A61K 39/12 424/204.1 |
| 2014/0056933 A1 | 2/2014 | Renner et al. | |
| 2017/0065704 A1 | 3/2017 | Kapre | |
| 2017/0274063 A1 | 9/2017 | Carra et al. | |

FOREIGN PATENT DOCUMENTS

WO WO2016/022916 2/2016

OTHER PUBLICATIONS

Tissot et al. PLOS vol. 5, No. 3 Mar. 2010.*
Search Report and Written Opinion for PCT App. No. PCT/US16/51264, dated Dec. 1, 2016.
Jason D. Fiedler et al., "Engineered Mutations Change the Structure and Stability of a Virus-Like Particle" *Biomacromolecules*, 13 (8), pp. 2339-2348 (2012).
Schwarz et al., Development of virus like particles for diagnostic and prophylactic biomedical applications, Wiley Interdisciplin Rev. Nanomed Nanobiotechnol. Sep. 2015 7(5):722-735.
Beterams et al., Packaging of up to 240 subunits of a 17 kDa nuclease into the interior of recombinant hepatitis B virus capsids FEBS Letters 481 (2000) 169-176.
A.C. Tissot et al., Versatile Virus Like Particle Carrier for Epitope Based Vaccines, PlusOne 5(3):e9809 (Mar. 2010).

* cited by examiner

*Primary Examiner* — Jana A Hines
*Assistant Examiner* — Khatol S Shahnan Shah
(74) *Attorney, Agent, or Firm* — Remenick PLLC

(57) ABSTRACT

The invention is directed to vaccines comprising capsular polysaccharides conjugated to one or more components of virus like particles (VLP), and methods for the administration of and methods for the manufacture of vaccines of the invention. Preferably vaccines of the invention generate a therapeutically effective response in an individual in need thereof to multiple strains and/or serotypes of the same or of different infectious agents. Preferably such vaccines generate a therapeutically effective immune response to all pathogenic strains and/or serotypes of the same infectious agent. In particular, the invention is directed to methods and compositions for the cost efficient administration of a vaccine to a patient in need thereof exposing the patient's immune system to only the immunogenic components that are likely to be beneficial for the generation of a protective immunological response, both efficacy and safety are increased and cost effectively.

19 Claims, No Drawings

MULTIVALENT VLP CONJUGATES

REFERENCE TO RELATED APPLICATIONS

This application claims priority to U.S. Provisional Application No. 62/216,646 entitled "Multivalent VLP Conjugates" filed Sep. 10, 2015, the entirety of which is hereby incorporated by reference.

BACKGROUND

1. Field of the Invention

The present invention provides compositions, methods and vaccines that are multivalent for use against viral, bacterial and others diseases, in particular, compositions and methods for the manufacture of multivalent conjugate vaccines using VLP's.

2. Description of the Background

Infections caused by viral, bacterial or other agents occur in a variety of animals. Infections are generally species specific and classified into distinct groups based on the host that they infect which can include multiple serotypes. Multivalent vaccines have been developed in an attempt to vaccinate against all or the most likely serotypes of the infectious agent. A multivalent pneumococcal polysaccharide vaccine, Prevnar 13, has been used in preventing pneumococcal disease. Prevnar 13 contains thirteen pneumococcal serotypes, serotypes 1, 3, 4, 5, 6A, 6B, 7F, 9V, 14, 18C, 19A, 19F, and 23F. There still exist nine additional serotypes that could be pathogenic, and thus, the Prevnar 13 vaccine does not address infections caused by these additional nine serotypes. Another problem exists in that these new serotypes do not have a human host. As vaccine development takes many years, there exists an urgency to develop a suitable vaccine as soon as possible.

Virus-like particles (VLPs) have been shown to be useful as vaccines against a variety of infectious agents including viral and bacterial infections. VLP's are formed from the self-assembly of structural proteins of selected groups of viruses. These proteins self-assembly into a capsule, but, as none of the replicating nucleic acids are present, the VLP cannot replicate virus genome and create more or otherwise infectious virus particles. VLPs are strictly non-infectious and generally harmless to the environment.

When VLPs are formed in the presence of an antigenic molecule, the VLP's become delivery vehicles for the antigen or, in other words, effective vaccines. VLPs can possess an antigenicity similar to the parent virus from which the structural components were obtained or derived and therefore useful as vaccines against that particular virus infection. VLP's are generally useful as vaccines by possessing antigen within the components of the VLP. This allows for foreign antigens to be exposed on their surfaces. Other VLPs have been used as carriers for foreign antigens, including non-protein antigens, via chemical conjugation. However, decorating VLPs with target-antigens by genetic fusion or chemical modification is time-consuming and often leads to capsid misassembly or antigen misfolding, hindering generation of protective immunity.

Presently available vaccines, such as vaccines against *Streptococcus pneumoniae*, involve a multivalent polysaccharide conjugate vaccine using a protein carrier. Currently there is a limitation on the number of antigen conjugates which creates a zone of no protection to the balance serotypes. As the current vaccine prevents infection caused by pathogens specific to the vaccine antigens, pathogens not antigenically represented in the vaccine become more predominant. In such a circumstance there would be no protective vaccine available for a considerable time which would include the time required to identify the new pathogen, to identify and characterize target antigens, and to develop a new vaccine. Also the current issue is the single protein used as a carrier protein. The protein component in the conjugate is twice the polysaccharide quantity and starts becoming a huge number with an increase in valency. For multivalent vaccine containing many serotypes, the protein load for the patient can be enormous. For example, assuming that the polysaccharide antigenic portion would be required at two micrograms per dose per serotype and four micrograms of carrier protein per dose per serotype, a 23 valent vaccine would create a protein load of about 92 micrograms in a dose that could be disastrous for the patient.

Accordingly, a need exists for a vaccine that does not induce a protein overload, but is protective against all pathogenic strains and/or serotypes of a particular infectious microorganism.

SUMMARY OF THE INVENTION

The present invention overcomes the problems and disadvantages, associated with current strategies and designs and provides novel vaccines and methods for fighting infectious diseases and, in particular, all pathogenic strains of a particular disease.

One embodiment of the invention is directed to vaccines comprising one or more, and preferably multiple immunogenic antigens obtained or derived from the same or a different infectious agent coupled with virus like particles (VLP). Preferably the immunogenic antigens are polysaccharides (PS) representing multiple or all pathogenic serotypes of the infectious agent. Preferably the virus like particles are obtained or derived from hepatitis virus, human papilloma virus, respiratory syncytial virus, flavivirus or combinations thereof. Preferably the multiple polysaccharides are covalently coupled via conjugation to one or more components of the virus like particles. Preferably the conjugation involves coupling via a cyanylating agent such as, for example, 1-cyano-4-(dimethylamino)-pyridinium tetrafluoroborate (CDAP), 1-cyanobenzotriazole (1-CBT), 2-cyanopyridazine-3(2H)-One (2-CPO), 1-cyanoimidazole (1-CI), 1-cyano-4-pyrrolidinopyridinium tetrafluorborate (CPPT) or a combination thereof.

Preferably the infectious agent comprises a virus, a bacterium, or a parasite. Preferably, the virus comprises one or more of enterovirus, hepatitis virus, human immunodeficiency virus (HIV), human papilloma virus (HPV), influenza virus, pertussis virus, rubella virus, tetanus virus, varicella zoster virus (VZV), flavivirus, West Nile virus, dengue virus, tick-borne encephalitis virus, yellow fever virus, Zika virus and combinations thereof. Preferably the bacterium comprises one or more of chlamydia, clostridium, diphtheria, meningococcal, streptococcal, staphylococcal, pneumococcal, bacillus or combinations thereof. Preferably the parasite comprises giardia, plasmodium or a combination thereof. Preferably the VLP are obtained or derived from a single virus, such as for example, a hepatitis virus which may be recombinantly produced, but may be produced from multiple different viruses. Preferably the polysaccharide is covalently coupled to one or more components of the virus like particles, and obtained and/or derived from one or more, two or more or all of the serotypes 1, 2, 3, 4, 5, 6B, 7F, 8, 9N, 9V, 10A, 11A, 12F, 14, 15B, 17F, 18C, 19A, 19F, 20, 22F, 23F, and 33F of *Streptococcus pneumoniae*. Vaccines of the invention may comprise an adjuvant such as, for example, aluminum hydroxide with phosphate buffer, or may not require an adjuvant to generate a therapeutically effective immune response against the infectious agent upon administration to a patient.

Preferably the vaccine is therapeutically effective against multiple serotypes (e.g., multivalent polysaccharide-VLP conjugate vaccine) and generates the humoral and/or a cellular immune response against one or more infectious agents. Preferably the therapeutically effective vaccine is a vaccine the provided protection to an individual against a subsequent infection and/or provides therapeutic treatment to an infected individual. Preferably the therapeutically effective vaccines of the invention provide protection against multiple serotypes of the infectious agent. Preferably the therapeutically effective immune response comprises a humoral and/or a cellular immune response against the infectious agent.

Another embodiment of the invention is directed to methods of preventing or treating infection by the infectious agent comprising administering the vaccine of the invention to a patient. Preferably administration comprises intramuscular injection, intraperitoneal injection, intravenous injection, intranasal, oral or transdermal. Preferably the patient is an infant, a toddler, an adolescent, an adult or a senior.

Another embodiment of the invention is directed to methods of manufacturing the vaccine of the invention comprising: mixing components of virus like particles with multiple immunogenic antigens of the same or different infectious agents; conjugating the components of the virus like particle with multiple immunogenic antigens of the same or different infectious agents; and forming a vaccine of conjugated virus like particles. Preferably the conjugated VLP are lyophilized. Vaccines of the invention may or may not contain adjuvant. Preferred adjuvants, when used include, for example, aluminum hydroxide and a phosphate buffer. Vaccines of the invention may further contain a stabilizing agent. Preferred stabilizing agents comprise, for example, sorbitol and/or degraded gelatin.

Other embodiments and advantages of the invention are set forth in part in the description, which follows, and in part, may be obvious from this description, or may be learned from the practice of the invention.

DESCRIPTION OF THE INVENTION

Conventional procedures for the development of multivalent vaccines involve multivalent polysaccharides in a protein carrier. Because of the large number of strains and/or serotypes of a particular infectious agent, the protein load can be enormous and, therefore, making them such constructions useable as vaccines. When valency (i.e. the number of strains, serotypes of the infectious agent) is reduced to address protein/antigen overloads, zones of no protection are created to pathogenic serotypes unrepresented in the vaccine. As a consequence, pathogens not antigenically represented in the vaccine become more predominant in the otherwise vaccinated population. Although short term protection of some of the population may be achieved, the longer term prospect can be the rapid and aggressive generation of infections attributed to unvaccinated strains with the expected pathologies and complications that now may be otherwise untreatable.

It was surprisingly discovered that virus-like particles (VLP) conjugated with multiple different polysaccharides (PS) representing the serotype variations of a particular infectious agent can be utilized as effective multivalent vaccines. Surprisingly, even with a large number of conjugated PS there is little to no capsid misassembly or antigen misfolding that would otherwise hinder generation of protective immunity from the resulting vaccination. Although adjuvant may be added, it was also surprisingly discovered that added adjuvant is not necessary for a therapeutically effective and protective vaccine. A therapeutically effective vaccine is a vaccine the provided protection to an individual against a subsequent infection and/or provides therapeutic treatment to an infected individual. As the VLP has adjuvant property, a vaccine of the invention has a tremendous immune-potentiating effect but with a lower dose quantity than would be otherwise be necessary. The conjugation reaction reduces the amount of antigenic material needed for a protective vaccination, preferably by about one half or less. In addition, the lack of a need for adjuvant, further reduces the amount of material necessary for a protective a vaccination. The reduction of both antigenic materials needed and overall quantity required allows for the production of multivalent vaccines that are protective against large number of serotypes of a particular infectious agent, and also vaccines that are protective against multiple different infectious agents. One of the significant advantages attributed to the reduction of antigen needed and overall quantity of vaccine material is that vaccines of the invention can be administered to children which generally require a lower dose of antigen and/or vaccine quantity as compared with adult vaccines.

One embodiment of the invention is directed to VLP vaccines comprising one or more and preferably multiple antigens of the same or multiple different infectious agents. Vaccines of the invention allow for adding all of the pathogenic serotypes, preferably of polysaccharides, making a complete vaccine against the pathogen. The immunogenicity of such a combination is higher than that created from conventional multivalent vaccines, and with a reduced dose quantity which in turn would reduce the protein load to the patient. This is of particular importance where the conjugate vaccine includes $CRM_{197}$. The quantity of $CRM_{197}$ needed for a vaccine of the invention is quantitatively less by one half or more as compared to conventional vaccines. Thus, VLP vaccines of the invention avoid the major complications that prevent development of a complete vaccine, and without creating either a toxic overdoes or any side effects attributed to the administration of high doses of an antigen and/or large volumes of a vaccine.

Virus-like particles resemble viruses, but are non-infectious and do not contain viral genetic material. VLPs can self-assemble from expression of the viral structural proteins, such as, for example, envelope or capsid proteins in vitro or in culture. VLP portions are preferably created from virus or virus-like agents that infect humans, bacteria, parasites, fungus, plant, and/or other hosts. Preferred VLP that contain viral proteins include, but are not limited to VLP's purified from or derived from hepatitis virus (e.g., Hep A, B, C, D and/or E), human papilloma virus (HPV), parvoviruses (e.g. 20 adeno-associated virus), respiratory syncytial virus, retroviruses (e.g. HIV), influenza virus and combinations thereof. VLPs of the invention are preferably obtained or derived from Hepatitis B virus (Hep B) and composed of the small HBV derived surface antigen (HBsAg). VLPs can be produced in a variety of cell culture systems including mammalian cell lines, insect cell lines, yeast, and plant cells. Preferably the VLP portion is a universally recognized portion of the infectious agent and may be purified, synthesized, created as fusion proteins, and/or recombinantly produced. Preferably the antigenic portions of the VLP are commercially available and shown to be safe for use in vaccines having a recognized safety profile.

The immunogenic agent of the VLP comprises an antigen or other structure that stimulates an immune response in an individual. Immunogenic agents include, but are not limited to peptides, proteins, lipids, fatty acids, polysaccharides, lipopolysaccharides. Typically, immunogenic agents are surface antigens of an infectious particle. Antigens may be specific for a particular infectious agent or combination of agents such as, for example, viral infectious agents (e.g., enterovirus, hepatitis virus, human immunodeficiency virus {HIV}, human papilloma virus {HPV}, influenza virus, pertussis virus, rubella virus, tetanus, varicella virus {VZV}, flavivirus, West Nile virus, dengue virus, tick-borne encephalitis virus, yellow fever virus, Zika virus), bacterial infectious agents (e.g., chlamydia, clostridium, diphtheria, meningococcal, streptococcal, staphylococcal, pneumococcal), parasitic infectious agents (e.g., giardia, malaria {plasmodium}), and/or an agent that causes sepsis or septicaemia. Preferably the immune response is sufficient to protect the individual from subsequent infections for a period of time. Preferably the vaccine is effective and protects a patient from infection for six months or greater, one year or greater, two years or greater, five years of greater, or ten years or greater The immune response generated in response to the immunogenic agent of the invention generates a humoral immune response, a cellular immune response, or preferably both in the individual. Preferred cellular response includes a T cell response, and/or a phagocytic response, and also preferably a memory cell response.

VLP of the invention may be fused, conjugated or otherwise attached (e.g., covalently or non-covalently bonded) with antigenic portions of an infectious agent. Preferably, the VLP of the invention are conjugated with multiple polysaccharides (PS) of one or more infectious agents, and preferably, capsular polysaccharides of the same or of different infectious agents such as, for example, infectious microorganism that infect humans. Conjugated vaccines may be created by covalently attaching a VLP to a PS using activating agents such as, for example, cyanylating reagents, such as, for example, 1-cyano-4-(dimethylamino)-pyridinium tetrafluoroborate (CDAP) or other well-known cyanylating reagent (e.g., 1-cyanobenzotriazole {1-CBT}, 2-cyanopyridazine-3(2H)-One {2-CPO}, 1-cyanoimidazole {1-CI}, 1-cyano-4-pyrrolidinopyridinium tetrafluorborate {CPPT}). Processes for conjugation may include linker compounds and are very well know and commercially available (Lees, et al., "Activation of Soluble Polysaccharides with 1-Cyano-4-Dimethylamino Pyridinium Tetrafluoroborate For Use in Protein-Polysaccharide Conjugate Vaccines and Immunological Reagents," Vaccine, Vol. 14, No. 3 (1996), pp. 190 198; U.S. Pat. No. 9,044,517). By coupling VLPs to multiple and different PS (which may be of the multiple serotypes of the same infectious agent or multiple infectious agents), both strong and broad immunity against an infection agent can be obtained as VLP's are inherently immunologic.

Preferably VLPs of the invention are coupled to all of the pathogenic forms (e.g., serotypes, strains, types, species, subspecies) of a particular infectious microorganism, or at least all that are relevant to afford protection to an individual and/or particular population. PS may be conjugated to the fully formed VLP or the structural components of the VLP and the VLP formed after conjugation.

In one embodiment, a conjugate vaccine can be created by covalently attaching an antigenic polysaccharide portion (which may have otherwise been found to be poorly antigenic) to a carrier protein, thereby creating the immunological attributes of the carrier also for the attached antigen. So the conjugated polysaccharide/protein carrier induces a T cell response, but would be for both the constituents. For example, with cross-reactive antigen (e.g., $CRM_{197}$) as carrier, there is often an enormous unwanted antibody generation towards the $CRM_{197}$. Such is not the case when using VLPs as the immune response generated is protective against the particular disease.

A VLP carrier protein conjugated with PS being highly immunogenic reduces the dose quantity otherwise required, while maintaining the immune-potentiating power at reduced dose. Such a conjugate is stable and, optionally, can be formulated with aluminum hydroxide and phosphate buffer for increased adsorption. Stability of VLP vaccines can be further supplemented, without increasing the antigenic load, with the addition of sugar alcohols such as, for example, sorbitol, gelatins and preferably chemically and/or mechanically degraded gelatins (e.g., with average molecular weights of ten kilodaltons {kD} or less). Stabilizing agents that are useful with VLP vaccines are disclosed in U.S. patent application Ser. No. 15/257,143 entitled "*VLP Stabilized Vaccine Compositions*" and filed Sep. 6, 2016, which is specifically incorporated by reference.

A preferred multivalent conjugate vaccine of the invention comprises a plurality of capsular polysaccharides of *Streptococcus pneumoniae* conjugated with a recombinant hepatitis VLP. The vaccine may be effective against any or more, or all serotypes of *Streptococcus pneumoniae* (e.g., 1, 2, 3, 4, 5, 6, 7, 8, 9 10, 11, 12, 13, 14, 15, 16, 17, 18, 19, 20, 21, 22, or 23 serotypes) Preferably the vaccine comprises at least two different capsular polysaccharides representing at least two different serotypes of *Streptococcus pneumoniae*, more preferably at least five, more preferably at least ten, more preferably at least fifteen, more preferably at least twenty, and even more preferably at least twenty three. The resulting vaccine is effective as a universal adult and also infant vaccine at least because the dosage required would be lower than currently available multivalent pneumococcal vaccine and would be well tolerated by children and infants. The protein requirement as carrier would be around 23 micrograms which is close to the adult dose. As no excess protein would be injected, such vaccine would be much safer than is currently available. This allows for creation of a larger numbered polyvalent vaccine which otherwise due to large protein quantity may not be efficacious for all components.

Other infections agents include one or more of the eleven clusters of *Staphylococcus aureus* and related sub-species, the twenty serotypes of *Pseudomonas aeruginosa*, at least three of which are clinically relevant (serotypes 03, 06 and 011), O antigen, K antigen and H antigen serotypes of *Eschericia coli* including pathogenic serotypes O157:H7, O104:H4, O121, O26, O103, O111, O145, and O104:H21, and the various pathogenic strains and/or serotypes of *Klebsiella, Enterobacter, Serratia, Citrobacter. Salmonella, Listeria, Shigella, Campylobacter*, and *Mycobacterium*.

Another embodiment of the invention is directed to the treatment and/or prevent of infection attributed to an infectious agent by the administration of the VLP vaccine of the invention to a patient. Effective methods of administration of vaccines of the invention include, but are not limited to administration via a patch (e.g., dermal patch), injection (e.g., intra-muscular, intra-peritoneal, intra-organ, intra-venous, intra-cerebral), inoculation, oral or direct gastrointestinal tract administration, transdermal absorption, a vaccine gun or jet injector or, preferably, through transdermal absorptions using dissolving or soluble biodegradable needle arrays. Preferably the vaccine of the invention is given as an intradermal injection or via a dermal patch without aluminum adjuvants. Due to this route the dose quantity would be further reduced and yet having the vaccine as effective and safe as the larger dose. Preferably the vaccine is maintained as a liquid, but the liquid may be lyophilized and stored as a dry powder until use wherein the powder is rehydrated in an appropriate carrying agent (aqueous or non-aqueous) for administration to the individual. Administration is preferable by injection which may be intra peritoneal (i.p.), intra muscular (i.m.), and/or intra venous (i.v.), or localized to the site of an infection.

Preferably the vaccines of the invention as liquids or powders are stable at 4° C. or greater, 15° C. or greater, 25° C. or greater, 37° C. or greater, 40° C. or greater, 50° C. or greater, or 100° C. or greater. Also preferably, the vaccines of the invention as liquids or powers are stable at 15° C. or less, more preferably to 0° C. or less, more preferably to minus 20° C. or less, and more preferably to minus 50° C. or less. Also preferably, stability of the vaccines is maintained for six month or greater, for eight months or greater or for twelve months or greater. Preferably the vaccines of the invention are stable through varying temperatures over time which may include multiple freezing and thawing.

Another embodiment of the invention is directed to methods for the administration of vaccines of the invention to patients in need thereof for treating or preventing an infection. The method comprises administering a therapeutically effective amount of the vaccine of the invention to a mammal, comprising determining the therapeutically effective amount of the vaccine to be administered that provides therapy to an infected patient and/or protection from infection. The therapeutically effective amount is typically determined by based on the weight of the mammal and the strength or responsiveness of the patient's immune system and can be determined by those skilled in the art. The therapeutically effective amount is administered to a patient in need thereof, which may be to treat an active or suspected infection or prevent an infection. The vaccine may have been obtained from a lyophilized powder and reconstituted to an aqueous or non-aqueous liquid prior to administration to the patient. Preferably the vaccine is administered as a liquid, which may be intra-muscular, intra-peritoneal, or intra-venous, and the patient may be an infant, a toddler, an adolescent, an adult or a senior. Surprisingly, the vaccine of the invention does not generate side effects such as redness or inflammation at the injection site, and does not generate a generalized fever or inflammation, or other unwanted side effects for the patient. Preferably an immunologically effective vaccine contains only the fully formed VLPs containing multiple immunogenic agents, and nothing further such as, for example, no added adjuvants.

Another embodiment of the invention is directed to method for the manufacture of vaccines of the invention. Structural components of viruses are obtained by methods well known to those skilled in the art and exclusive of any nucleic acid material that would allow the components and resulting particles to replicate. Predetermined molar amounts of the structural components are mixed, preferably at room temperature or below, with approximately equivalent molar amounts of one or more immunogenic agents and one or more stabilizing agents of the invention, such that the VLPs encapsulate the one or more immunogenic agents and the one or more stabilizing agents in roughly equivalent amounts. The fully formed VLPs are separated from unformed VLPs and free structural and other materials preferably by filtration, centrifugation or another method known to those skilled in the art, thereby creating fully formed VLPs containing one more immunogens and one or more stabilizing agents. The fully formed VLPs may be stored as an aqueous (e.g., water or saline) or non-aqueous (e.g., oils, fatty acids) mixture, or lyophilized and stored as a powder. Preferably storage until use is without significant loss of immunogenic activity and, for example, may be for one month or longer, four months or longer, six months or longer, or more preferably one year or longer and at ambient temperatures, whether as a liquid or a powder. Storage of vaccine without loss of immunogenic activity may also be at less than ambient temperature such as, for example, at 20° C. or less, at 10° C. or less, at 4° C. or less, or at 0° C. or less.

The following examples illustrate embodiments of the invention, but should not be viewed as limiting the scope of the invention.

Example 1 VLP Conjugate Vaccine Against *Streptococcus Pneumonia*

VLPs are obtained from the structural components of hepatitis virus and covalently conjugated with a capsular polysaccharide derived from *Streptococcus pneumoniae*. The conjugated VLPs are coupled with *Streptococcus pneumoniae* immunogenic peptides, which are isolated from the microorganism or recombinantly prepared. The conjugate is formulated with aluminum hydroxide and phosphate buffer as an adjuvant and for increased tissue adsorption, in accordance with the preparation of conventional Hep B vaccines. The resulting conjugate vaccine is stable for long periods of time (e.g., at least 1-6 months at 4° C. or at least 12-24 months when lyophilized). Due at least in part to the immune-potentiating power of the conjugate, the vaccine is administered to a mammal at a dose of one microgram per serotype. With 23 serotypes, the protein load of the carrier is a total of about 23 micrograms per vaccination, which is close to the adult dose. When administered to mammal with an active immune system (e.g., an adult human), the patient generates a protective immune response to *Streptococcus pneumoniae* in the form of both a humoral and a cellular response, and with no risk of protein overload.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. The term comprising, where ever used, is intended to include the terms consisting and consisting essentially of. Furthermore, the terms comprising, including, and containing are not intended to be limiting. It is intended that the specification and examples be considered exemplary only with the true scope and spirit of the invention indicated by the following claims.

The invention claimed is:

1. A vaccine against multiple serotypes of an infectious agent comprising virus like particles obtained or derived from hepatitis virus coupled to multiple polysaccharides each polysaccharide representing a serotype of the infectious agent with little to no misassembly or misfolding, wherein the infectious agent is *Streptococcus pneumoniae*.

2. The vaccine of claim 1, wherein the multiple polysaccharides are covalently coupled via conjugation to one or more components of the virus like particles.

3. The vaccine of claim 2, wherein the conjugation involves coupling via a cyanylating agent.

4. The vaccine of claim 3, wherein the cyanylating agent comprises 1-cyano-4-(dimethylamino)-pyridinium tetrafluoroborate (CDAP), 1-cyanobenzotriazole (1-CBT), 2-cyanopyridazine-3 (2H)-One (2-CPO), 1-cyanoimidazole (1-CI), 1-cyano-4-pyrrolidinopyridinium tetrafluorborate (CPPT) or a combination thereof.

5. The vaccine of claim 1, wherein the multiple polysaccharides are obtained and/or derived from one or more of the serotypes 1, 2, 3, 4, 5, 6B, 7F, 8, 9N, 9V, 10A, 11A, 12F, 14, 15B, 17F, 18C, 19A, 19F, 20, 22F, 23F, and 33F of *Streptococcus pneumoniae*.

6. The vaccine of claim 1, wherein the multiple polysaccharides are obtained and/or derived from two or more of the serotypes 1, 2, 3, 4, 5, 6B, 7F, 8, 9N, 9V, 10A, 11A, 12F, 14, 15B, 17F, 18C, 19A, 19F, 20, 22F, 23F, and 33F of *Streptococcus pneumoniae*.

7. The vaccine of claim 1, wherein the multiple polysaccharides are obtained and/or derived from the serotypes 1, 2, 3, 4, 5, 6B, 7F, 8, 9N, 9V, 10A, 11A, 12F, 14, 15B, 17F, 18C, 19A, 19F, 20, 22F, 23F, and 33F of *Streptococcus pneumoniae*.

8. The vaccine of claim 1, which does not require an adjuvant to generate a therapeutically effective response.

9. The vaccine of claim 1, further comprising an adjuvant.

10. The vaccine of claim 9, wherein the adjuvant comprises aluminum hydroxide with phosphate buffer.

11. The vaccine of claim 1, which upon administration to a patient, generates a therapeutically effective immune response against the infectious agent.

12. The vaccine of claim 11, wherein the therapeutically effective immune response comprises protection to an individual against a subsequent infection of the infectious agent and/or therapeutic treatment to an individual infected by the infectious agent.

13. The vaccine of claim 11, wherein the therapeutically effective immune response provides protection against infection by multiple serotypes of the infectious agent.

14. The vaccine of claim 11, wherein the therapeutically effective immune response comprises a humoral and/or a cellular immune response against the infectious agent.

15. The vaccine of claim 6, wherein the multiple polysaccharides are obtained and/or derived from five or more of the serotypes 1, 2, 3, 4, 5, 6B, 7F, 8, 9N, 9V, 10A, 11A, 12F, 14, 15B, 17F, 18C, 19A, 19F, 20, 22F, 23F, and 33F of *Streptococcus pneumoniae*.

16. The vaccine of claim 15, wherein the multiple polysaccharides are obtained and/or derived from ten or more of the serotypes 1, 2, 3, 4, 5, 6B, 7F, 8, 9N, 9V, 10A, 11A, 12F, 14, 15B, 17F, 18C, 19A, 19F, 20, 22F, 23F, and 33F of *Streptococcus pneumoniae*.

17. The vaccine of claim 16, wherein the multiple polysaccharides are obtained and/or derived from fifteen or more of the serotypes 1, 2, 3, 4, 5, 6B, 7F, 8, 9N, 9V, 10A, 11A, 12F, 14, 15B, 17F, 18C, 19A, 19F, 20, 22F, 23F, and 33F of *Streptococcus pneumoniae*.

18. The vaccine of claim 17, wherein the multiple polysaccharides are obtained and/or derived from twenty or more of the serotypes 1, 2, 3, 4, 5, 6B, 7F, 8, 9N, 9V, 10A, 11A, 12F, 14, 15B, 17F, 18C, 19A, 19F, 20, 22F, 23F, and 33F of *Streptococcus pneumoniae*.

19. The vaccine of claim 18, wherein the multiple polysaccharides are obtained and/or derived from twenty three or more of the serotypes 1, 2, 3, 4, 5, 6B, 7F, 8, 9N, 9V, 10A, 11A, 12F, 14, 15B, 17F, 18C, 19A, 19F, 20, 22F, 23F, and 33F of *Streptococcus pneumoniae*.

\* \* \* \* \*